United States Patent [19]

Kubo et al.

[11] Patent Number: 4,547,365
[45] Date of Patent: * Oct. 15, 1985

[54] WAVING LOTION FOR COLD WAVING

[75] Inventors: Sanae Kubo, Sagamihara; Fumiaki Nakamura, Yokohama, both of Japan

[73] Assignee: Shiseido Company Ltd., Tokyo, Japan

[*] Notice: The portion of the term of this patent subsequent to Oct. 15, 2002 has been disclaimed.

[21] Appl. No.: 545,816

[22] Filed: Oct. 27, 1983

[30] Foreign Application Priority Data

Nov. 8, 1982 [JP] Japan .................... 57-195799

[51] Int. Cl.[4] .................. A61K 7/09; A61K 7/11; A61L 13/00
[52] U.S. Cl. .................. 424/71; 424/72; 424/76
[58] Field of Search .................. 424/71, 72, 76

[56] References Cited

U.S. PATENT DOCUMENTS

| | | | |
|---|---|---|---|
| 4,024,223 | 5/1977 | Noda et al. | 424/235 |
| 4,030,512 | 6/1977 | Papantoniou et al. | 424/71 |
| 4,041,150 | 8/1977 | Karjala | 424/DIG. 2 |
| 4,267,166 | 5/1981 | Yajima | 424/76 |
| 4,358,286 | 11/1982 | Grollier et al. | 424/74 |

FOREIGN PATENT DOCUMENTS 521369 7/1953 France .................. 424/71

OTHER PUBLICATIONS

Chem. Abst. #98:124514p (Asama).
Chem. Abst. #94:36133a (Yajima).

*Primary Examiner*—Albert T. Meyers
*Assistant Examiner*—Freda Abramson
*Attorney, Agent, or Firm*—Sprung Horn Kramer & Woods

[57] ABSTRACT

An aqueous waving lotion for cold waving comprising:
(i) a mercapto compound, (ii) at least one compound selected from the group consisting of the compounds having the general formulae (I) to (XX),

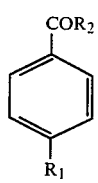
(I)

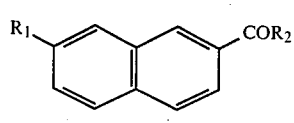

(II)

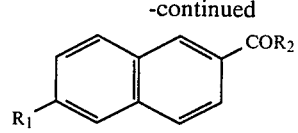

(III)

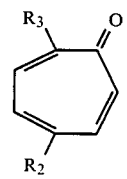

(IV)

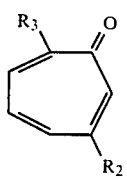

(V)

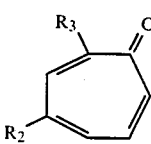

(VI)

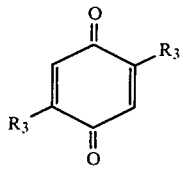

(VII)

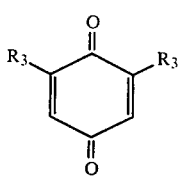

(VIII)

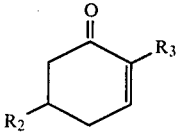

(IX)

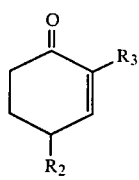

(X)

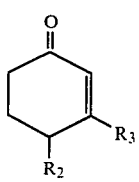

(XI)

(Abstract continued on next page.)

-continued

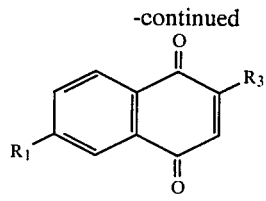 (XII)

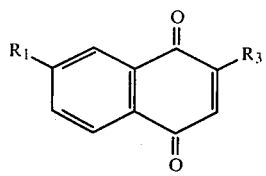 (XIII)

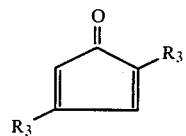 (XIV)

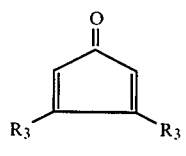 (XV)

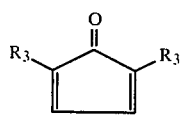 (XVI)

-continued

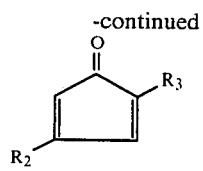 (XVII)

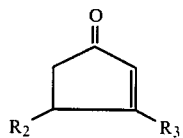 (XVIII)

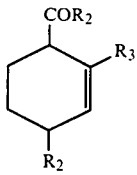 (XIX)

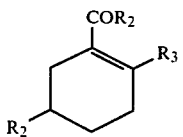 (XX)

wherein $R_1$ is hydrogen or an electron attractive group, $R_2$ is hydrogen or an alkyl group having 1 to 4 carbon atoms, and $R_3$ is hydrogen, a hydroxyl group, or a methyl group, and (iii) a cyclodextrin.

This aqueous waving lotion has no substantial mercaptan odor and generates no substantial or less of a mercaptan odor when applied to the hair.

6 Claims, No Drawings

WAVING LOTION FOR COLD WAVING

BACKGROUND OF THE INVENTION

1. Field of the Invention

The present invention relates to a waving lotion for cold waving. More specifically, it relates to a waving lotion for cold waving having no substantial mercaptan odor and generating no substantial or less of a mercaptan odor when applied to the hair, which is formulated by incorporating (a) p-nitro acetophenone methyl-β-naphtyl ketone, or a similar compound and (b) a cyclodextrin into a conventional waving lotion.

2. Description of the Prior Art

As is well known in the art, permanent waving lotions are composed of (i) waving lotions containing, as a main component, reducing agents, that is, mercapto compounds such as thioglycolic acid and cysteine and (ii) neutralizers containing oxidizing agents such as sodium bromate and hydrogen peroxide. However, the use of conventional waving lotions involves problems in that conventional waving lotions per se have a specific mercaptan odor and that conventional waving lotions generate a large amount of mercaptan having an extremely unpleasant odor when applied to the hair. Thus, the use of conventional waving lotions is not desirable for consumers and beauticians from the viewpoints of environmental health.

Various attempts have been made to eliminate the above-mentioned unpleasant mercaptan odor. Typical conventional methods for eliminating the unpleasant mercaptan odor are incorporated into waving lotions to thereby sensuously mask the unpleasant mercaptan odor. However, the amount of mercaptan generated during the application processing of waving lotions to the hair is very large and mercaptan odor is a typically unpleasant odor regulated as a polluting odor. Accordingly, mercaptan odor included in, for example, the entire space of beauty salons cannot be completely masked by perfume-utilizing masking methods. On the other hand, some people dislike the perfumes having strong odor generally used in the masking methods due to their strong and heavy odor.

For the above-mentioned reasons, it is considered that the mercaptan odor per se must be eliminated from waving lotions in order to fundamentally solve the above-mentioned problems of unpleasant odor. However, in order to solve the above-mentioned problems, if deodorants capable of suppressing the vaporization of mercaptans through chemical reactions are incorporated into waving lotions, or if deodorants are separately applied to the hair simultaneous with the application of waving lotions, mercaptans such as thioglycolic acid and cysteine contained as a main component in waving lotions are reacted with the deodorants to inhibit the desirable reducing effect essential for waving lotions and, therefore, the waving effect or power of waving lotions is disadvantageously decreased. Furthermore, after the deodorants are consumed, undesirable mercaptans are again generated.

SUMMARY OF THE INVENTION

Accordingly, the object of the present invention is to fundamentally eliminate the above-mentioned generation of an unpleasant odor from waving lotions and to provide a waving lotion having no substantial mercaptan odor and generating no substantial or less of a mercaptan odor when applied to the hair.

Other objects and advantages of the present invention will be apparent from the following description.

In accordance with the present invention, there is provided an aqueous waving lotion for cold waving comprising: (i) a mercapto compound, (ii) at least one compound selected from the group consisting of the compounds having the general formulae (I) to (XX),

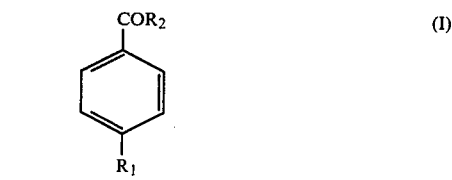
(I)

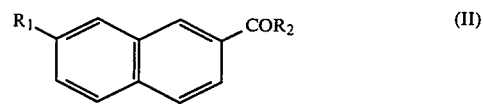
(II)

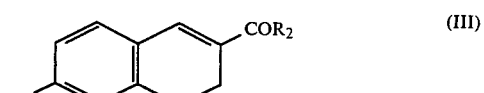
(III)

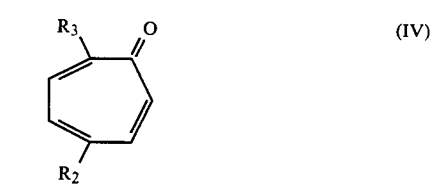
(IV)

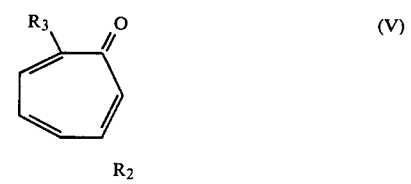
(V)

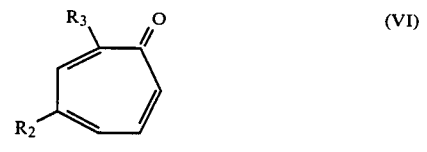
(VI)

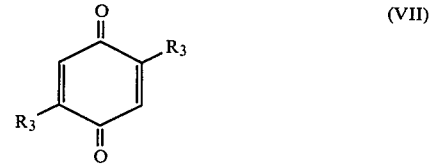
(VII)

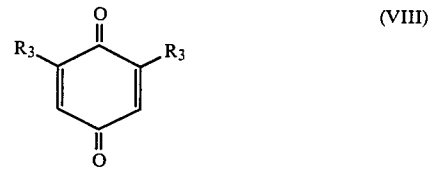
(VIII)

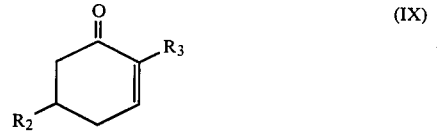
(IX)

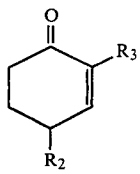 (X)

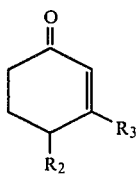 (XI)

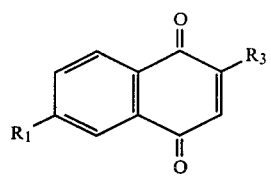 (XII)

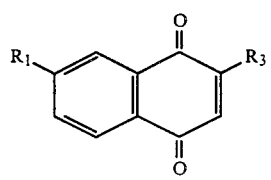 (XIII)

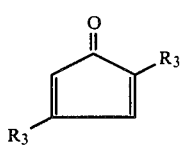 (XIV)

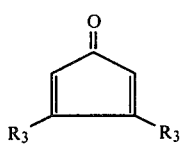 (XV)

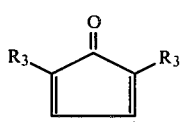 (XVI)

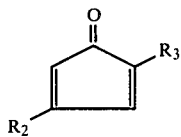 (XVII)

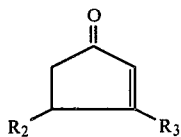 (XVIII)

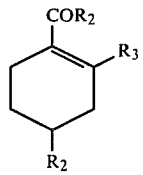 (XIX)

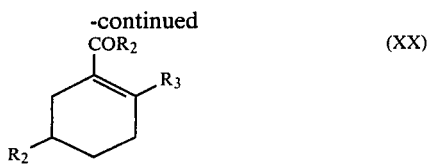 (XX)

wherein $R_1$ is hydrogen or an electron attractive group such as $COCH_3$, $COC_2H_5$, $COC_3H_7$, $OCOCH_3$, $OCOC_2H_5$, $OCOC_3H_7$, Cl, Br, I, $SCOCH_3$, SCN, CN, $CF_3$, $N^+(CH_3)_3$, or $NO_2$, $R_2$ is hydrogen or an alkyl group having 1 to 4 carbon atoms such as a methyl group, an ethyl group, or an isopropyl group, and $R_3$ is hydrogen, a hydroxyl group, or a methyl group, and (iii) a cyclodextrin.

DESCRIPTION OF THE PREFERRED EMBODIMENTS

When the above-mentioned compounds (ii) and (iii) are incorporated into aqueous waving lotions containing, as a main component, a mercapto compound according to the present invention, only mercaptan causing unpleasant bad odor can be selectively captured to effectively prevent vaporization of the unpleasant odor, without decreasing the desired fundamental reducing effect or power, based on thioglycolic acid, cysteine, and other mercapto compounds, of the aqueous waving lotion (i.e., the mercapto compounds are not substantially consumed by the above-mentioned compounds (ii) and (iii)).

The compounds (ii) usable in the preparation of the present aqueous waving lotion are those having the above-mentioned general formulae (I) to (XX). These compounds may be used alone or in any mixture thereof. The preferable compounds are: p-hydroxy acetophenone, 1-acetyl-4-carboxy methyl benzene, 1-acetyl-4-carboxy ethyl benzene, p-diacetyl benzene, and p-nitro acetophenone included in the general formula (I), β-methyl naphthyl ketone included in the general formula (III), hinokitiol included in the general formula (IV), 2-cyclohexanone and carvone included in the general formula (X), and 2-hydroxy-1,4-naphthoquinone included in the general formula (XII).

The cyclodextrins (iii) usable in the preparation of the present aqueous waving lotion are α-, β-, γ-, or δ-cyclodextrin, or any mixture thereof. Typical cyclodextrins are α-, β-, and γ-cyclodextrins.

The compounds (ii) and (iii) should be incorporated into the waving lotion at a mole ratio of (ii):(iii)=1:9 to 1:1, preferably 1:4 to 1:1.

When the amount of the compound (ii) is less than 1 mole based on 9 moles of the compound (iii) or is more than 1 mole based on 1 mole of the compound (iii), the desired effect to eliminate the unpleasant mercaptan odor from the waving lotion or during the processing of the waving lotion cannot be obtained.

The compounds (ii) having the general formulae (I) to (XX) and the compounds (iii) (i.e., cyclodextrins) are desirably incorporated into the aqueous waving lotion of the present invention in an amount of, in total, 0.0002% to 40% weight, preferably 0.1% to 5% by weight. The use of too small an amount of the compounds (ii) and (iii) does not exhibit the desired odor elimination effect, whereas the use of too large an amount of the compounds (ii) and (iii) results in no substantial increase in the unpleasant mercaptan odor elimination effect.

The compounds (ii) and (iii) may be separately incorporated into the aqueous waving lotion according to the present invention. However, the compounds (ii) and (iii) are preferably incorporated into the aqueous waving lotion after being subjected to one of the following treatments:

(1) The compounds (ii) having the general formulae (I) to (XX) are dissolved with or without heating in an organic solvent such as ethyl alcohol, isopropyl alcohol, propylene glycol, dipropylene glycol, glycerine, sorbitol, or other similar polyols and, then, are mixed with cyclodextrin or an aqueous solution thereof having an appropriate concentration;

(2) The compounds (ii) having the general formulae (I) to (XX) are dissolved in a volatile organic solvent such as methyl alcohol, ethyl alcohol, isopropyl alcohol, ethyl ether, acetone, or methyl ethyl ketone and, then are mixed with a cyclodextrin or an aqueous solution thereof having an appropriate concentration, followed by vaporizing the organic solvent or water under heating at an ordinary or reduced pressure or under an ambient temperature at an ordinary or reduced pressure; and (3) The compounds (ii) having the general formulae (I) to (XX), cyclodextrin or an aqueous solution thereof, and water are mixed together at a temperature of less than 50° C. while being stirred or while being subjected to an ultrasonic treatment.

The mechanism of the unpleasant mercaptan odor elimination of the above-mentioned compounds (ii) and (iii) is not clearly understood, but it would seem that, without prejudice to the present invention, inclusion complexes are formed between the compounds (ii) and (iii) in the aqueous mixture and these inclusion complexes do not attack thioglycolic acid, cysteine, and other mercapto compounds, but are selectively reacted with mercaptan. We believe that, since the compounds (ii) having the general formulae (I) to (XX) have one or more carbonyl groups therein, the inclusion complexes with the compounds (iii) are formed in the aqueous waving lotion taking into consideration the molecular sizes and the locations of the substituents in the compounds (ii).

The aqueous waving lotion of the present invention may contain, as a main component, any conventional mercapto compound. Examples of such mercapto compounds are thioglycolic acid, thioglycolates such as sodium thioglycolate, potassium thioglycolate, ammonium thioglycolate, monoethanol amine thioglycolate, glycerol monothioglycolate, thiolactic acid and its salts, and L-Alginine thioglycolate, cysteine, cysteine derivatives such as N-acetyl-L-cysteine, and cystein ethylester, and salts, such as hydrochloric acid and sulfuric acid salts, of the cysteine derivatives. These mercapto compounds may be used alone or in any mixtures thereof. Although there is no specific limitation in the content of the mercapto compounds in the waving lotion, the mercapto compounds are preferably incorporated into the waving lotion in an amount of 2% to 10% by weight, more preferably 3% to 7% by weight, based on the total weight of the waving lotion.

The aqueous waving lotion of the present invention may optionally contain any conventional ingredients used in conventional waving lotions. Examples of such conventional ingredients are hair softening agents such as ammonia, alkylol amines, and ammonium salts, oils such as liquid paraffines, squalene, fatty alcohols, triglyceride, esters, silicone oils, and lanolin, surfactants such as nonionic surfactants (e.g., polyoxyethylene alkyl ether), anionic surfactants (e.g., sodium lauryl sulfate, sodium laurate), and cationic surfactants (e.g., stearyl trimethyl ammonium chloride), sequestrants such as ethylene diamine tetra acetate (EDTA), colorants such as Guaiazulene, Quinoline yellow WS (D. and C. Yellow No. 10), Rhodamine B (D. and C. Red No. 19), perfumes, preservatives such as methyl parabene, sodium benzoate, and other agents such as water soluble polymers, cationic polymers, polypetide, amino acids, and humectants.

The waving lotion according to the present invention may be applied to the hair in the same manner as conventional waving lotions. After waving the hair, the hair is treated with conventional neutralizers containing, as a main component, bromate such as sodium bromate, potassium bromate, hydrogen peroxide, sodium percarbonate, sodium perborate in any conventional manner.

EXAMPLE

The present invention now will be further illustrated by, but is by no means limited to, the following examples, in which all percentages and parts are expressed on a weight basis unless otherwise specified.

EXAMPLE 1

The compounds listed in Table 1 below were incorporated into the following standard formulation to prepare waving lotions.

| Standard formulation Composition | % by weight |
| --- | --- |
| 50% Aqueous ammonium thioglycolate | 13.0 |
| Ammonium bicarbonate | 5.0 |
| Tetrasodium EDTA*[1] | 0.1 |
| Compound listed in Table 1 | see Table 1 |
| Purified water | balance |

*[1]Ethylene diamine tetraacetic acid

The aqueous waving lotions thus obtained were evaluated as follows.

1. Hair waving effect

Hair was wounded around rods and, then, was treated with the waving lotions prepared above, followed by treatment with a neutralizer.

The composition of the neutralizer was as follows:

| Components | % by weight |
| --- | --- |
| Sodium bromate | 5.0 |
| Disodium phosphate, dibasic | 0.1 |
| Potassium phosphate, monobasic | 0.4 |
| Sodium benzoate | 0.1 |
| Purified water | balance |

The waving effects of the waving lotions were evaluated from the formed coils. It is considered that, the smaller the diameter (mm) of the resultant coil is, the larger the waving power is.

2. Odor of waving lotion

The hydrogen sulfide generated in the upper spaces of the waving lotion containers was quantitatively determined by gas chromatography (FPD). The waving lotions were allowed to stand at room temperature for 5 months.

The hydrogen sulfide contents were organoleptically evaluated as follows:

300 ppm or more: Very strong mercaptan odor
150 ppm to 300 ppm: Strong mercaptan ordor
70 ppm to 150 ppm: Weak mercaptan odor
0 to 70 ppm: No substantial mercaptan odor 3. Reaction odor in hair A 0.5 g amount of hair was mixed with 1.0 g of the waving lotion. The mixture was placed in a 400 ml plastic container and was allowed to stand at a temperature of 30° C. for 20 minutes. After 20 minutes, the odor was determined by means of gas chromatography (FPD) and by smelling.

As is clear from Run Nos. 12 to 15 in Table 1, the mercaptan odor of the waving lotions and the reaction odor of the waving lotions in the hair were eliminated or suppressed by incorporating a mixture of p-nitro acetophenone or p-diacetyl benzene and cyclodextrin into the waving lotions. When p-nitro acetophenone or p-diacetyl benzene and cyclodextrin were separately incorporated into the waving lotions, the desired effects were obtained, as shown in Run Nos. 8 to 11, although they were not as effective as those in Run Nos. 12 to 15.

EXAMPLE 2

The effects of various compounds represented by the general formulae (I) to (XX) on the elimination of the unpleasant mercaptan odor were evaluated in the same manner as in Run Nos. 12 to 15 of Example 1.

The results are shown in Table 2.

As is clear from the results shown in Table 2, the compounds having $R_1$ of electron attractive groups, as in Nos. 6 and 8, in the general formulae (I) to (XX) were effective, whereas the compounds having $R_1$ of electron donating groups as in Nos. 2 to 4 were not effective as compared with the compounds having $R_1$ of hydrogen. As $R_2$ in the general formulae, hydrogen was effective as shown in No. 7, and the effect was decreased in the cases of $CH_3$ and $C_2H_5$ in this order (see Nos. 5 and 9). In the case of $R_2$ being $C_5H_{11}$, the effect was remarkably decreased as shown in No. 10 and no substantial advantage was obtained by the incorporation thereof into waving lotions. In addition to the benzene ring as in Nos. 5 to 10, cyclic conjugated ketones as in Nos. 11 and 12 were effective as a mother nucleus.

TABLE 1

| No. | Compound incorporated into waving lotion | Appearance of waving lotion | pH | Waving effect (mm) | Odor of waving lotion H2S (ppm) | Reaction odor with hair H2S (ppm) |
|---|---|---|---|---|---|---|
| 1 | No addition | Crystal clear | 8.1 | 13.04 | 149 | 350 |
| 2 | p-Nitro acetophenone 0.06% | Crystallization | 8.0 | 13.11 | 143 | 353 |
| 3 | p-Diacetyl benzene 0.06% | " | 8.0 | 13.13 | 149 | 361 |
| 4 | p-Nitro acetophenone 0.06% + Dipropylene glycol 2%*1 | " | 8.1 | 13.74 | 115 | 351 |
| 5 | p-Diacetyl benzene 0.06% + Dipropylene glycol 2%*1 | " | 8.1 | 14.15 | 108 | 372 |
| 6 | β-Cyclodextrin 1.14% | Substantially transparent | 8.2 | 13.54 | 155 | 370 |
| 7 | Celdex CH—30H*2 5% | Crystal clear | 8.1 | 13.35 | 165 | 360 |
| 8 | β-Cyclodextrin 1.14% + p-Nitro acetophenone 0.06%*3 | Crystallization | 8.1 | 13.13 | 180 | 200 |
| 9 | Celdex CH—30H 5% + p-Nitro acetophenone 0.06%*3 | " | 8.0 | 13.22 | 93 | 280 |
| 10 | β-Cyclodextrin 1.14% + p-Diacetyl benzene 0.06%*3 | " | 8.1 | 13.16 | 105 | 250 |
| 11 | Celdex CH—30H 5% + p-Diacetyl benzene 0.06%*3 | " | 8.1 | 13.51 | 81 | 253 |
| 12 | β-Cyclodextrin 1.14% + p-Nitro acetophenone 0.06% + Dipropylene glycol 2%*4 | Substantially transparent | 7.9 | 12.31 | 20 | 113 |
| 13 | Celdex CH—30H 5% + p-Nitro acetophenone 0.06% + Dipropylene glycol 2%*4 | Crystal clear | 7.9 | 12.64 | 17 | 125 |
| 14 | β-Cyclodextrin 1.14% + p-Diacetyl benzene 0.06% + Dipropylene glycol 2%*4 | Substantially transparent | 8.2 | 12.06 | 25 | 105 |
| 15 | Celdex CH—30H 5% + p-Diacetyl benzene 0.06% + Dipropylene glycol 2%*4 | Crystal clear | 8.2 | 11.89 | 20 | 93 |

*1 Both compounds were dissolved in water at a temperature of 80° C. for 5 minutes and, then, were incorporated into the waving lotion.
*2 An aqueous solution containing 10 to 12% of a mixture of α-, β-, and γ-cyclodextrins manufactured by NIHON SHOKUHIN KAKO CO., LTD.
*3 Both compounds were separately incorporated into the waving lotion.
*4 p-Nitro acetophenone or p-diacetyl benzene was dissolved in dipropylene glycol. β-Cyclodextrin or Celdex CH—30H was mixed with a portion of water (15%) and, then, the resultant mixture was further mixed with the dipropylene glycol solution obtained above at a room temperature, while stirring. The mixture was incorporated into the waving lotion.

TABLE 2

| Run No. | General formula | Compound R1 | R2 | R3 | Incorporated amount (%) | β-Cyclodextrin (%) | pH | Waving effect (mm) | Odor of waving lotion H2S (ppm) | Reaction odor with hair H2S (ppm) |
|---|---|---|---|---|---|---|---|---|---|---|
| 1 | — | — | — | — | — | — | 8.0 | 12.1 | 155 | 380 |
| 2 | COR2 (benzene ring with R1) | OH | CH3 | — | 0.1 | 1.14 | 8.0 | 11.9 | 143 | 350 |
| 3 | | C2H5 | CH3 | — | " | " | 7.9 | 11.8 | 115 | 348 |
| 4 | | CH3 | CH3 | — | " | " | 7.8 | 12.9 | 93 | 330 |
| 5 | | COCH3 | CH3 | — | " | " | 7.8 | 12.1 | 20 | 110 |
| 6 | | OCOC2H5 | CH3 | — | " | " | 7.8 | 12.5 | 17 | 129 |
| 7 | | H | H | — | " | " | 7.8 | 12.4 | 15 | 129 |
| 8 | | NO2 | H | — | " | " | 7.8 | 12.1 | 16 | 99 |
| 9 | | H | C2H5 | — | " | " | 7.8 | 11.8 | 40 | 132 |
| 10 | | H | C5H11 | — | " | " | 7.9 | 11.9 | 73 | 300 |
| 11 | (cycloheptatrienone with R2, R3) | — | C3H7 | OH | " | " | 7.8 | 12.0 | 28 | 138 |

TABLE 2-continued

| Run No. | Compound General formula | $R_1$ | $R_2$ | $R_3$ | Incorporated amount (%) | β-Cyclo-dextrin (%) | pH | Waving effect (mm) | Odor of waving lotion $H_2S$ (ppm) | Reaction odor with hair $H_2S$ (ppm) |
|---|---|---|---|---|---|---|---|---|---|---|
| 12 | (cyclohexenone structure with $R_2$, $R_3$) | — | H | H | " | " | 7.9 | 12.1 | 34 | 136 |

EXAMPLE 3

A waving lotion having the following composition was prepared:

| Composition | % by weight |
|---|---|
| 50% Aqueous ammonium thioglycolate | 12.5 |
| Monoethanolamine | 1.0 |
| 28% Aqueous ammonia | 2.0 |
| Tetrasodium EDTA | 0.1 |
| Sodium lauryl sulfate | 0.2 |
| p-Nitro acetophenone | 0.06 |
| Celdex CH-30H | 5.00 |
| Dipropylene glycol | 2.0 |
| Purified water | balance |

The waving lotion was prepared as follows. p-Nitro acetophenone was dissolved in dipropylene glycol at 80° C. for 5 minutes. After cooling, the solution was added to an aqueous Celdex CH-30H solution, which was obtained by dissolving Celdex CH-30H in a portion (about 15%) of the purified water. The mixture was stirred at room temperature to form a solution and, then, the other components listed above were added thereto while stirring, to obtain a clear waving solution.

The above components were mixed at room temperature to prepare the waving lotion.

A neutralizer having the following composition was prepared by mixing the components at room temperature.

| Composition | % by weight |
|---|---|
| Sodium bromate | 5.0 |
| Buffer (i.e., disodium phosphate) | q.s. |
| Preservative (i.e., sodium benzoate) | q.s. |
| Purified water | balance |

According to a conventional processing method of permanent waving lotion, the waving lotion was first applied in an amount of 80 ml/person and, then, the neutralizer was applied in an amount of 100 ml/person. The mercaptan odor was very weak when the cap was taken out from the container of the waving lotion ($H_2S$=120 ppm) and also when the waving lotion was applied ($H_2S$=18 ppm). Thus, the use of the compounds (ii) and (iii) was very effective for eliminating the unpleasant mercaptan odor. After the application of the neutralizer, good waves were found to have been formed when rods were removed. The resultant permanent wave was elastic and bright.

EXAMPLE 4

A waving lotion having the following composition was prepared.

| Composition | % by weight |
|---|---|
| 50% Aqueous ammonium thioglycolate | 13.0 |
| Ammonium bicarbonate | 5.0 |
| Trisodium EDTA | 0.1 |
| Cetyl alcohol | 0.5 |
| Polyoxyethylene oleyl ether (E.O. = 20 mole) | 0.1 |
| Sodium lauryl sulfate | 0.05 |
| Methyl-β-naphthyl ketone | 0.1 |
| β-cyclodextrin | 1.0 |
| Purified water | 41.25 |

The waving lotion was prepared as follows. Methyl-β-naphthyl ketone and β-cyclodextrin were dissolved in a portion of the purified water (10%) at a temperature of 48° C. to form a first aqueous solution. On the other hand, the cetyl alcohol, the polyoxyethylene oleyl ether, and the sodium lauryl sulfate were melted together at a temperature of 80° C. and, then, were mixed with a portion of the purified water (30%) heated to a temperature of 80° C. The mixture was cooled to a room temperature (about 25° C.), while stirring, to form a viscous white gel. The gel and the first solution were mixed with the other components at room temperature, while stirring, to obtain a viscous translucent white waving agent. The mole ratio of methyl-β-naphthyl ketone and β-cyclodextrin was 1:1.67.

The cold waving was carried out by using the above-prepared waving lotion and the neutralizer prepared in Example 3. As a result, no substantial mercaptan odor was smelt during the application ($H_2S$=123 ppm) and the ammonia odor was very weak. The wave thus obtained was bright and elastic. Only a weak ammonia odor was detected from the mouth of the waving lotion container and no substantial mercaptan odor was detected ($H_2S$=30 ppm).

EXAMPLE 5

A waving lotion having the following composition was prepared in the same manner as in Example 3.

| Composition | % by weight |
|---|---|
| 50% Aqueous ammonium thioglycolate | 13.0 |
| Monoethanolamine | 0.5 |
| Ammonium bicarbonate | 4.5 |
| Trisodium EDTA | 0.2 |
| Hinokitiol | 0.28 |
| Celdex CH-30H | 40.0 |
| Polyoxyethylene oleyl ether (E.O. = 15 mole) | 0.5 |
| Perfume | 0.1 |
| Colorant | q.s. |
| Propylene glycol | 1.0 |
| Purified water | balance |

The waving lotion was prepared as follows. The hinokitiol was dissolved in the propylene glycol at a temperature of 80° C. This solution was added, together with the Celdex CH-30H, to the purified water while stirring at room temperature. The resultant solution was mixed with the other components at room temperature to obtain a transparent waving lotion. The mole ratio of the hinokitiol and the cyclodextrin was 1:2.33.

A mercaptan odor and an ammonia odor during the application of the waving lotion to the hair as well as a remaining odor in the hair were not substantially detected ($H_2S=132$ ppm). The elastic wave was formed. No substantial odor was detected from the mouth of the container ($H_2S=35$ ppm).

EXAMPLE 6

A waving lotion having the following composition was prepared in the same manner as in Example 4.

| Composition | % by weight |
| --- | --- |
| L-Cysteine | 5.0 |
| Monoethanolamine | 3.0 |
| Tetrasodium EDTA | 0.5 |
| Cetyl alcohol | 0.7 |
| Polyoxyethylene cetyl ether (E.O. = 10 mole) | 0.1 |
| 60% Aqueous stearyl trimethyl ammonium chloride | 0.2 |
| l-Carvone | 0.1 |
| Celdex CH-30H | 30.0 |
| Purified water | 60.5 |

The waving lotion was prepared as follows. The Celdex CH-30H was dissolved in the l-carvone at a temperature of 60° C. while stirring. The cetyl alcohol, the polyoxyethylene cetyl ether, and the stearyl trimethyl ammonium chloride were melted at a temperature of 80° C. and, then, was mixed with a portion of the purified water (about 40%) heated to a temperature of 80° C. The mixture was cooled to room temperature (about 25° C.), while stirring, to form viscous white gel. The solution and the gel thus prepared were mixed with the other components while stirring at room temperature. Thus, viscous white waving lotion was obtained. The mole ratio of the l-carvone and the cyclodextrin was 1:4.34.

The mercaptan odor and ammonia odor during the application of the waving lotion to the hair ($H_2S=165$ ppm) as well as the remaining mercaptan odor in the hair were weak since the odor was masked by l-carvone and only l-carvone odor was slightly detected. The elasticity of the hair thus obtained was less than the elasticity obtained in Examples 3, 4 and 5, but a desirable soft wave was obtained. Only a slight mercaptan odor was detected from the mouth of the container ($H_2S=55$ ppm).

EXAMPLE 7

A waving lotion having the following composition was prepared in the same manner as in Example 3.

| Composition | % by weight |
| --- | --- |
| 40% aqueous monoethanolamine thioglycolate | 10.0 |
| N—Acetyl-L-cystine | 3.0 |
| Tetrasodium EDTA | 0.5 |
| Methyl-β-naphtyl ketone | 0.15 |
| p-Nitro acetophenone | 0.03 |
| Celdex CH-30H | 20.0 |

-continued

| Composition | % by weight |
| --- | --- |
| Ammonium bicarbonate | 4.0 |
| Monoethanolamine | 1.0 |
| Polyoxyethylene oleyl ether (E.O. = 15 mole) | 0.5 |
| Perfume | 0.2 |
| Glycerine | 2.0 |
| Colorant | q.s. |
| Purified water | balance |

The waving lotion was prepared as follows. The methyl-β-naphtyl ketone and the p-nitro acetophenone were stirred into the glycerine at a temperature of 80° C. Then, after cooling, the purified water and the other components were added thereto at a temperature of 25° C. while stirring. Thus, a transparent waving lotion was obtained. The mole ratio of the total moles of the methyl-β-naphthyl ketone and p-nitro acetophenone to the cyclodextrin was 1:1.82.

Only a slight mercaptan odor ($H_2S=33$ ppm)(but a more noticeable ammonia odor) was smelt from the mouth of the waving lotion container. The reaction odor in the hair was weak ($H_2S=150$ ppm) and an elastic wave was formed.

EXAMPLE 8

A waving lotion having the following composition was prepared in the same manner as in Example 3.

| Composition | % by weight |
| --- | --- |
| 50% Aqueous ammonium thioglycolate | 12.5 |
| Monoethanolamine | 1.0 |
| 28% Aqueous ammonia | 2.0 |
| Tetrasodium EDTA | 0.1 |
| Cetyl alcohol | 0.5 |
| Polyoxyethylene cetyl ether (E.O. = 20 mole) | 0.1 |
| 60% Aqueous stearyl trimethyl ammonium chloride | 0.15 |
| p-Diacetyl benzene | 0.1 |
| Celdex CH-30H | 10.0 |
| Dipropylene glycol | 5.0 |
| Purified water | balance |

The waving lotion was prepared as follows. The p-diacetylbenzene was dissolved in the dipropylene glycol at a temperature of 80° C. for 5 minutes and, after cooling, the solution was mixed with the Celdex CH-30H at a temperature of 25° C., while stirring. Then, a portion (38.6%) of the purified water, the ammonium thioglycolate, the monoethanolamine, the aqueous ammonium, and the tetrasodium EDTA were dissolved in the solution obtained above at a temperature of 25° C., while stirring. On the other hand, the cetyl alcohol, the polyoxyethylene cetyl ether, and the stearyl trimethyl ammonium chloride were melted upon heating at a temperature of 80° C. The molten mixture was added to the remainder of the purified water previously heated to a temperature of 80° C. The mixture was cooled to room temperature (about 25° C.) to obtain a viscous white gel. The gel thus obtained was mixed with the solution obtained above at room temperature, while stirring, to prepare a viscous white waving lotion. The mole ratio of the p-diacetyl benzene and the cyclodextrin was 1:1.57.

Cold waving was carried out by using the above-prepared waving lotion and the neutralizer prepared in Example 3. No substantial mercaptan odor was detected during the application of the waving lotion to the hair ($H_2S=90$ ppm) and an elastic wave was obtained. No substantial mercaptan odor was detected from the mouth of the waving lotion container ($H_2S=22$ ppm).

We claim:

1. In an aqueous waving lotion for cold waving comprising (i) a mercapto compound, the improvement wherein such composition further contains (ii) at least one compound selected from the group consisting of the compounds having the general formulae (I) to (XX),

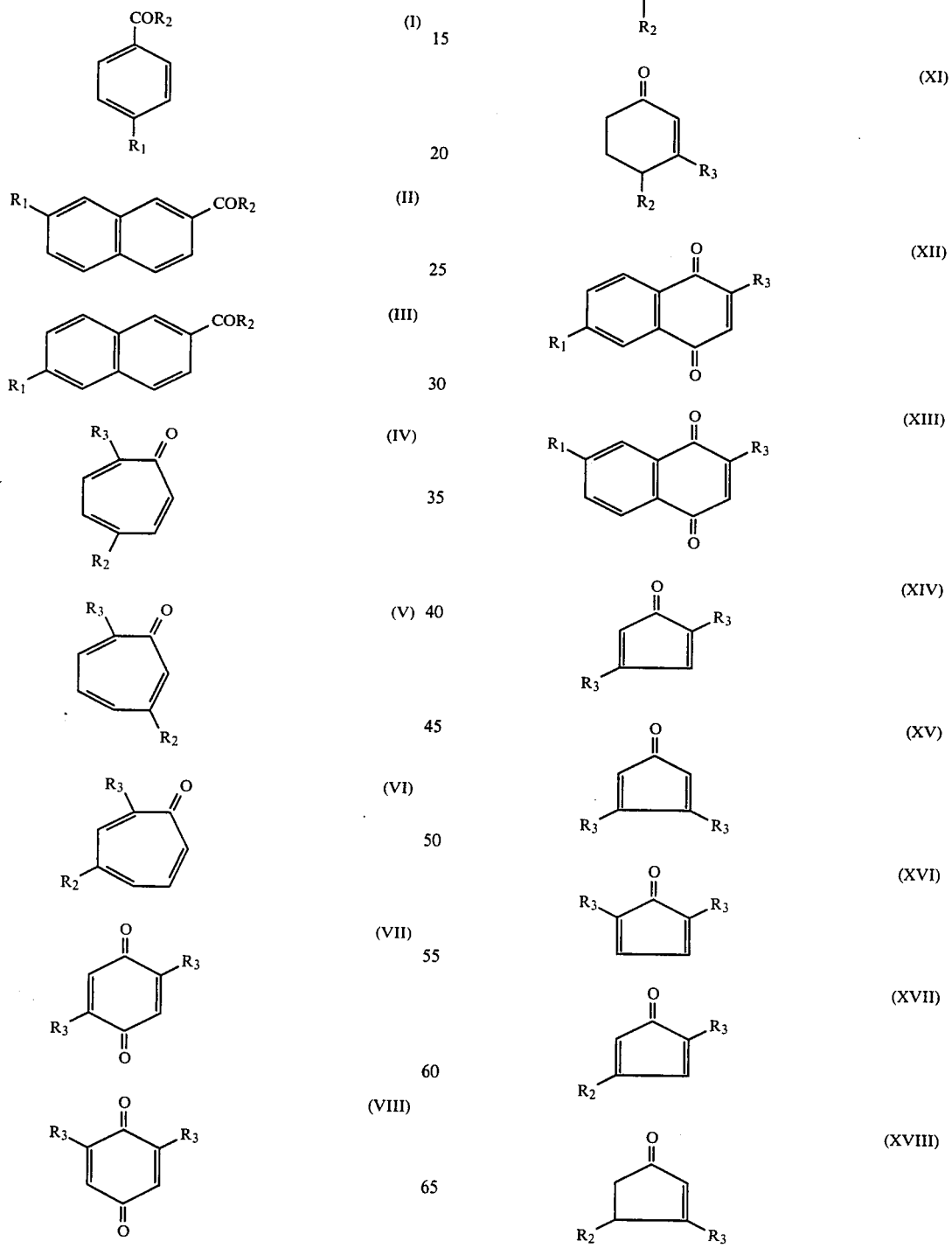

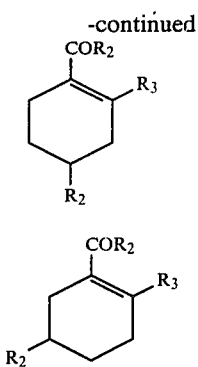

wherein $R_1$ is hydrogen, $COCH_3$, $COC_2H_5$, $COC_3H_7$, $OCOCH_3$, $OCOC_2H_5$, $OCOC_3H_7$, Cl, Br, I, $SCOCH_3$, SCN, CN, $CF_3$, $N^+(CH_3)_3$, or $NO_2$, $R_2$ is hydrogen or an alkyl group having 1 to 4 carbon atoms, and $R_3$ is hydrogen, a hydroxyl group, or a methyl group, and (iii) at least one cyclodextrin compound selected from the group consisting of α-, β-,, γ-, and δ-cyclodextrins, said compounds (ii) and (iii) being contained, in total, in an amount of 0.0002% to 40% by weight based on the total weight of the aqueous waving lotion and the mole ratio of the compound (ii) to the cyclodextrin (iii) in the aqueous waving lotion being 1:9 to 1:1, compound (ii) being incorporated into the aqueous waving lotion as a mixture thereof with compound (iii) after dissolving in an organic liquid.

2. An aqueous waving lotion as claimed in claim 1, wherein the content of the mercapto compound in the waving lotion is 2% to 10% by weight.

3. An aqueous waving lotion as claimed in claim 1, wherein the mercapto compound (i) is at least one compound selected from the group consisting of thioglycolic acid, sodium thioglycolate, potassium thioglycolate, ammonium thioglycolate, L-Alginine thioglycolate, monoethanolamine thioglycolate, glycerol monothioglycolate, thiolactic acid, cysteine, N-acetyl-L-cysteine, cysteine ethyl ester, and hydrochloric acid and sulfuric acid salts of N-acetyl-L-cysteine and cysteine ethyl ester.

4. An aqueous waving lotion as claimed in claim 1, wherein the mole ratio of the compounds (ii) and (iii) is (ii):(iii)=1:4 to 1:1.

5. An aqueous waving lotion as claimed in claim 1, wherein the compound (ii) is at least one compound selected from the group consisting of p-hydroxy acetophenone, 1-acetyl-4-carboxy methyl benzene, 1-acetyl-4-carboxy ethyl benzene, p-diacetyl benzene, and p-nitro acetophenone included in the general formula (I), β-methyl naphthyl ketone included in the general formula (III), hinokitiol included in the general formula (IV), 2-cyclohexanone and carvone included in the general formula (X), and 2-hydroxy-1,4-naphthoquinone inluded in the general formula (XII).

6. An aqueous waving lotion as claimed in claim 1, wherein the cyclodextrin compound is β-cyclodextrin or a mixture of α-, β-, and γ-cyclodextrins.

* * * * *